(12) United States Patent  (10) Patent No.: US 7,863,254 B2
Renshaw  (45) Date of Patent: Jan. 4, 2011

(54) COMPOUNDS FOR THE TREATMENT OF PSYCHIATRIC OR SUBSTANCE ABUSE DISORDERS

(75) Inventor: Perry F. Renshaw, Bedford, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 10/427,306

(22) Filed: May 1, 2003

(65) Prior Publication Data

US 2003/0220291 A1 Nov. 27, 2003

Related U.S. Application Data

(62) Division of application No. 09/810,109, filed on Mar. 15, 2001.

(60) Provisional application No. 60/189,727, filed on Mar. 16, 2000, provisional application No. 60/189,811, filed on Mar. 16, 2000, provisional application No. 60/189,728, filed on Mar. 16, 2000.

(51) Int. Cl.
  *A01N 43/04* (2006.01)
  *A61K 31/70* (2006.01)
(52) U.S. Cl. ............................................. 514/49
(58) Field of Classification Search .................. 514/46, 514/49, 564
  See application file for complete search history.

(56) References Cited

U.S. PATENT DOCUMENTS

| | | | |
|---|---|---|---|
| 4,027,017 A | 5/1977 | Hata et al. | |
| 4,048,316 A | 9/1977 | Penn | |
| 4,115,576 A | 9/1978 | Penn | |
| 4,386,077 A | 5/1983 | Borgo | |
| 4,704,361 A | 11/1987 | Miccoli et al. | |
| 4,764,603 A | 8/1988 | Zappia et al. | |
| 4,999,382 A | 3/1991 | Wurtman et al. | |
| 5,179,126 A | 1/1993 | Wurtman et al. | |
| 5,278,176 A | 1/1994 | Lin | |
| 5,409,946 A | 4/1995 | Garvey et al. | |
| 5,472,958 A | 12/1995 | Gunn, Jr. et al. | |
| 5,635,486 A | 6/1997 | Yamamoto et al. | |
| 5,691,320 A | 11/1997 | von Borstel et al. | |
| 5,691,365 A | 11/1997 | Crooks et al. | |
| 5,888,532 A | 3/1999 | Pritsos et al. | |
| 5,919,789 A | 7/1999 | Dyke et al. | |
| 5,958,896 A | 9/1999 | Renshaw et al. | |
| 5,977,174 A | 11/1999 | Bradley et al. | |
| 6,103,703 A | 8/2000 | Renshaw et al. | |
| 6,132,724 A * | 10/2000 | Blum | 424/725 |
| 6,153,653 A | 11/2000 | Shashoua | |
| 6,258,794 B1 | 7/2001 | Renshaw | |
| 6,277,855 B1 | 8/2001 | Yerxa | |
| 6,284,268 B1 | 9/2001 | Mishra et al. | |
| 6,319,953 B1 | 11/2001 | Carlson et al. | |
| 6,331,568 B1 | 12/2001 | Horrobin | |
| 6,410,522 B1 | 6/2002 | Ruenberg | |
| 6,503,951 B2 | 1/2003 | Pischel et al. | |
| 6,541,043 B2 | 4/2003 | Lang | |
| 6,608,064 B2 | 8/2003 | McLean et al. | |
| 6,624,195 B2 | 9/2003 | Horrobin | |
| 6,696,495 B2 * | 2/2004 | Mueller | 514/646 |
| 6,706,764 B2 | 3/2004 | Kaddurah-Daouk et al. | |
| 6,727,231 B1 | 4/2004 | Page et al. | |
| 6,852,870 B2 | 2/2005 | Stoll | |
| 6,989,376 B2 | 1/2006 | Watkins et al. | |
| 7,026,301 B2 * | 4/2006 | Cardozo et al. | 514/50 |
| 7,053,064 B2 | 5/2006 | Lukas | |
| 7,601,701 B2 | 10/2009 | Lukas | |
| 2002/0019364 A1 | 2/2002 | Renshaw | |
| 2002/0028787 A1 | 3/2002 | Watkins et al. | |
| 2002/0182196 A1 | 12/2002 | McCleary | |
| 2003/0100844 A1 * | 5/2003 | Miller et al. | 600/549 |
| 2003/0114415 A1 | 6/2003 | Wurtman et al. | |
| 2003/0220291 A1 | 11/2003 | Renshaw | |
| 2003/0224435 A1 | 12/2003 | Seiwert | |
| 2003/0232827 A1 | 12/2003 | Meltzer et al. | |
| 2004/0102419 A1 | 5/2004 | Kaddurah-Daouk et al. | |
| 2004/0167093 A1 | 8/2004 | Lukas | |
| 2004/0176316 A1 | 9/2004 | Renshaw et al. | |
| 2004/0192732 A1 | 9/2004 | Pratt et al. | |
| 2004/0266659 A1 | 12/2004 | LaBerge | |
| 2005/0113449 A1 | 5/2005 | Renshaw | |
| 2005/0129710 A1 | 6/2005 | Renshaw et al. | |
| 2006/0128671 A1 | 6/2006 | Kaddurah-Daouk et al. | |

(Continued)

FOREIGN PATENT DOCUMENTS

DE 3400276 7/1985

(Continued)

OTHER PUBLICATIONS

Page et al., Proc. Natl Acad Sci USA, Oct. 1997, vol. 94(21), pp. 11601-11606.*

(Continued)

*Primary Examiner*—Traviss C McIntosh, III
(74) *Attorney, Agent, or Firm*—Clark & Elbing LLP

(57) ABSTRACT

The invention provides methods for treating or preventing psychiatric and substance abuse disorders, involving administration of a therapeutically-effective amount of a cytosine-containing or cytidine-containing compound, creatine-containing compound, adenosine-containing, or adenosine-elevating compound to a mammal.

10 Claims, 5 Drawing Sheets

U.S. PATENT DOCUMENTS

| | | |
|---|---|---|
| 2006/0217344 A1 | 9/2006 | Lukas |
| 2008/0132472 A1 | 6/2008 | Renshaw |
| 2008/0300214 A1 | 12/2008 | Lukas et al. |
| 2009/0054370 A1 | 2/2009 | Renshaw |
| 2009/0215714 A1 | 8/2009 | Renshaw et al. |
| 2010/0041620 A1 | 2/2010 | Renshaw et al. |
| 2010/0041621 A1 | 2/2010 | Renshaw et al. |

FOREIGN PATENT DOCUMENTS

| | | | |
|---|---|---|---|
| EP | 0 188647 A1 | | 7/1986 |
| EP | 0218190 A2 | | 4/1987 |
| EP | 0218190 B1 | | 11/1989 |
| EP | 0 431 758 A2 | | 6/1991 |
| EP | 0615750 | | 9/1994 |
| JP | 63-208524 | | 8/1988 |
| JP | 2-500372 | | 2/1990 |
| JP | 08-183737 | | 7/1996 |
| RU | 2128653 | | 4/1999 |
| WO | WO 89/03837 | | 5/1989 |
| WO | WO 93/14076 | | 7/1993 |
| WO | WO 99/26620 | | 6/1999 |
| WO | WO 00/06174 | * | 2/2000 |
| WO | WO 00/11952 | | 3/2000 |
| WO | WO 01/44265 A1 | | 6/2001 |
| WO | WO 01/72288 A2 | | 10/2001 |
| WO | WO 02/45583 | | 6/2002 |
| WO | WO 02/088159 | | 11/2002 |

OTHER PUBLICATIONS

Secades et al., Methods Find Exp Clin Pharmacol., vol. 17 Suppl B, Oct. 1995, pp. 1-54 (abstract provided with relevant teachings).*
Shekim et al., Psychopharmacol Bull. 1990;26(2):249-53.*
Goodman & Gilman's: The Pharmacological Basis of Therapeutics, 10th Edition, McGraw-Hill Medical Publishing Division, 2001, pp. 54-56, 57.*
US Surgeon General, "Overview of ADHD and its Treatments", US Office of the Surgeon General, Mental Health Matters, 2000-2001, pp. 1-6.*
Carlezon et al., "Antidepressant-Like Effects of Cytidine in the Forced Swim Test in Rats," *Biol. Psychiatry* 51:882-889 (2002).
Pleul et al., "Lithium Therapy and the Turnover of Phosphatidylcholine in Human Erythrocytes," *Euro. J. Clin. Pharmacol.* 31:457-462 (1986).
Stoll et al., "Choline in the Treatment of Rapid Cycling Bipolar Disorder," *Biol. Psychiatry* 40:382-388 (1996).
Agnoli, et al., "Efficacy of CDP choline in Chronic Cerebral Vascular Diseases (CCVD)," *Novel Biochemical, Pharmacological and Clinical Aspects of Cytidinediphosphocholine* Elsevier (1985) 305-315.
Babb et al., "Differential Effect of CDP-choline on Brain Cytosolic Choline Levels in Younger and Older Subjects as Measured by Proton Magnetic Resonance Spectroscopy," *Psychopharmacology* (1996) 127:88-94.
Boudouresques, et al., "Therapeutic Conduct in Light of a Cerebral Vascular Accident and the Use of CDP-choline," *International Symposium: Brain Suffering and Precursors of Phospholipids* pp. 1-12 (1980).
Brown et al., "CNS Complications of Cocaine Abuse: Prevalence, Pathophysiology, and Neuroradiology," *Am. J. Roentgenol.* (1992) 159:137-147.
Centrone et al., "Use of Citicoline in High Dosages in Acute Cerebrovascular Disease," *Minerva Med.* (1986) 77:371-373.
Chang et al., "Neurochemical Alterations in Asymptomatic Abstinent Cocaine Users: A Proton Magnetic Resonance Spectroscopy Study," *Biol. Psychiatry* (1997) 42:1105-1114.
Christensen et al., "Abnormal Cerebral Metabolism in Polydrug Abusers During Early Withdrawal: A $^{31}$P MR Spectroscopy Study," *Magn. Reson. Med.* (1996) 35:658-663.
Citicoline Sodium (CDP-Choline), *Investigator's Brochure*, Revised: Apr. 1994 by Interneuron Pharmaceuticals, Inc.
Cohen et al., "Decreased Brain Choline Uptake in Older Adults," *JAMA* (1995) 274:902-907.
English et al., "Elevated Frontal Lobe Cytosolic Choline Levels in Minimal or Mild AIDS Dementia Complex Patients: A Proton Magnetic Resonance Spectroscopy Study," *Biol. Psychiatry* (1997) 41:500-502.
Gallai et al., "Study of the P300 and Cerebral Maps in Subjects with Multi-Infarct Dementia Treated with Cytidine," *Psychopharmacology* (1991) 103:1-5.
Galletti et al., "Biochemical Rationale for the Use of CDP-choline in Traumatic Brain Injury. Pharmacokinetics of the Orally Administered Drug," *J. Neural. Sci.* (1991) 103:S19-S25.
Hoff et al., "Effects of Crack Cocaine on Neurocognitive Function," *Psychiatry Res.* (1996) 60:167-176.
Jacobs et al., "Cocaine Abuse: Neurovascular Complications," *Radiology* (1989)170:223-227.
Kaufman et al., "Cocaine-Induced Cerebral Vasoconstriction Detected in Humans with Magnetic Resonance Angiography," *JAMA* (1998) 279:376-380.
Kreek "Opiate and Cocaine Addictions: Challenge for Pharmacotherapies," *Pharmacol. Biochem. Behav.* (1997) 57:551-569.
Levin et al., "Improved Regional Cerebral Blood Flow in Chronic Cocaine Polydrug Users Treated with Buprenorphine," *J. Nucl. Med.* (1995) 36:1211-1215.
London et al., "Cerebral Glucose Utilization in Human Heroin Addicts: Case Reports from a Positron Emission Tomographic Study," *Res. Commun. Subst Abuse* (1989) 10:141-144.
Lukas et al., "Effects of Short-term Citicoline Treatment on Acute Cocaine Intoxication and Cardiovascular Effects," *Psychopharmacology* (2001) 157:163-7.
Maas et al., "Functional Magnetic Resonance Imaging of Human Brain Activation During Cue-induced Cocaine Craving," *Am. J. Psychiatry* (1998) 155:124-126.
McCance, "Overview of Potential Treatment Medications for Cocaine Dependence," *NIDA Res. Monogr.*, (1997) 175:36-72.
Moglia et al., "Citicoline in Patients with Chronic Cerebrovascular Diseases (CCVD): Quantitative EEG Study," *Curr. Ther. Res.* (1984) 36:309-313.
O'Rourke et al., "Effect of Chronic Cocaine Exposure on Carotid Artery Reactivity in Neonatal Rabbits," *Life Sci.* (1996) 59:119-130.
Peterson et al., "Neurovascular Complications of Cocaine Abuse," *J. Neuropsychiatry Clin. Neurosci.*, (1991) 3:143-149.
Renshaw et al., "Short-term Treatment with Citicoline (CDP-choline) Attenuates Some Measures of Craving in Cocaine-Dependent Subjects: A Preliminary Report," *Psychopharmacology* (1999) 142:132-8.
Saligaut et al., "Circling Behaviour in Rats with Unilateral Lesions of the Nigrostriatum Induced by 6-Hydroxydopamine: Changes Induced by Oral Administration of Cytidine-5'-Diphosphocholine," *Neuropharmacology* (1987) 26:1315-1319.
Self, et al., "Opposite Modulation of Cocaine-seeking Behavior by $D_1$- and $D_2$-like Dopamine Receptor Agonists," *Science* (1996) 271:1586-1589.
Sholar et al., "Concurrent Pharmacokinetic Analysis of Plasma Cocaine and Adrenocorticotropic Hormone in Men," *J. Clin. Endocrinol. Metab.* (1998) 83:966-968.
Tazaki et al., "Treatment of Acute Cerebral Infarction with a Choline Precursor in a Multicenter Double-Blind Placebo-Controlled Study," *Stroke* (1988) 19:211-216.
Teoh et al., "Acute Interactions of Buprenorphine with Intravenous Cocaine and Morphine: An Investigational New Drug Phase I Safety Evaluation," *J. Clin. Psychopharmacol.* (1993) 13:87-99.
Warner et al., "Pharmacotherapy for Opioid and Cocaine Abuse," *Med. Clin. North Am.* (1997) 81:909-925.
Weiss, "Metabolism and Actions of CDP-Choline as an Endogenous Compound and Administered Exogenously as Citicoline," *Life Sci.* (1995) 56:637-660.
Lukacsko et al., "Modulation of the Vasoconstrictor Response to Adrenergic Stimulation by Nucleosides and Nucleotides," *J. Pharmacol. Exp. Ther.* 222:344-349, 1982.

Malec et al., "Influence of Adenosinergic Drugs on Ethanol Withdrawal Syndrome in Rats" *Polish Journal of Pharmacology* 48:583-588, 1996—Abstract.

Monticone, G. F. et al., "On the Therapeutic Use of Nucleosides, Cytidine and Uridine in some, Neurological Diseases," *Minerva Medica* 57:4348-52, 1966, not in english.

Salvadorini et al., "Clinical Evaluation of CDP-Choline (NICHOLIN®): Efficacy as Antidepressant Treatment," *Current Therapeutic Research* 18:513-520, 1975.

Tomos et al., "Effect of Oral CDP-Choline on Experimental Withdrawal Syndrome," *Arzneim.-Forsh./Drug Res.* 33(11):1018-1021, 1983.

Wurtman et al., "Effect of Oral CDP-Choline on Plasma Choline and Uridine Levels in Humans," *Biochemical Pharmacology* 60:989-992, 2000.

Connolly et al., "Uridine and its Nucleotides: Biological Actions, Therapeutic Potentials," *TiPS* 20:218-225 (1999).

XP-002302971—RU 2003332, "Use of Uridine as Antidepressant—Shows its Reduced Toxicity and Elimination of Several Harmful Side Effects."

Bronk et al., "The Transport and Metabolism of Naturally Occurring Pyrimidine Nucleosides by Isolated Rat Jejunum", *Journal of Physiology* (395): 349-361 (1988).

Tucker et al. "Inhibition by Adenosine Analogs of Opiate Withdrawal Effects," *NIDA Res Monogr.* 49:85-91 (1984). (XP001208315).

Jørgensen et al., "Herpes simplex virus (HSV) antibodies in child psychiatric patients and normal children", Acta Psychiatr Scand Jul. 1982;66(1):42-49.

Nicolson et al., "Evidence for Mycoplasma ssp., Chlamydia pneunomiae, and human herpes virus-6 coinfections in the blood of patients with autistic spectrum disorders", J Neurosci Res Apr. 2007;85(5):1143-1148.

U.S. Appl. No. 12/704,964, Renshaw et al.

Adibhatla et al., "Citicoline Mechanisms and Clinical Efficacy in Cerebral Ischemia," J. Neurosci. Res. 70:133-139, 2002.

Ágren et al., "Creatinine and Creatine in CSF: Indices of Brain Energy Metabolism in Depression. Short Note," J. Neural. Transm. 74:55-59, 1988.

Agut et al., "Cytidine(5')Diphosphocholine Enhances the Ability of Haloperidol to Increase Dopamine Metabolites in the Striatum of the Rat and to Diminish Stereotyped Behavior Induced by Apomorphine," Neuropharmacology 23:1403-1406, 1984.

Alvarado et al., "1H Magnetic Resonance Spectroscopy (MRS) Assessment of the Effects of Eicosapentaenoic-Docosahexaenoic Acids and Choline-Inositol Supplementation on Children with Attention Deficit Hyperactivity Disorder (ADHD)," VITAE Academia Biómedica Digital Julio-Septiembre 2004 N° 20 [Available at http://vitae.ucv.ve/?rv=68] (pp. 1-18).

Ambrosini et al., "Antidepressant Treatments in Children and Adolescents: II. Anxiety, Physical, and Behavioral Disorders," J. Am. Acad. Child Adolesc. Psychiatry 32:483-493, 1993.

American Psychiatric Association, "Diagnostic and Statistical Manual of Mental Disorders: DSM-IV," American Psychiatric Association (Washington, D.C.), Entry for "Substance Dependence Criteria," pp. 181-183, 1994.

American Psychiatric Association, "Diagnostic and Statistical Manual of Mental Disorders: DSM-IV," American Psychiatric Association (Washington, D.C.), Entry for "Mood Episodes" and "Depressive Disorders," pp. 320-327, 339-349, 718, 1994.

Andreazza et al., "Oxidative Stress Markers in Bipolar Disorder: A Meta-Analysis," J. Affect. Disord. 111:135-144, 2008.

Beers et al., "The Merck Manual of Diagnosis and Therapy," Merck & Co, Inc., 17th Edition, Chapter 173: Sleeping Disorders, pp. 1409-1414, 1999.

Biederman et al., "Non-Stimulant Treatments for ADHD," Eur. Child Adolesc. Psychiatry 9:151-159, 2000.

Bishopp, "Interneuron's Citicoline Works for Moderate to Severe Stroke," BioWorld Today, Jul. 17, 1997, p. 3.

Budney et al., "Marijuana Abstinence Effects in Marijuana Smokers Maintained in Their Home Environment," Arch. Gen. Psychiatry 58:917-924, 2001.

Carlezon et al., "Antidepressant-Like Effects of Uridine and Omega-3 Fatty Acids are Potentiated by Combined Treatment in Rats," Biol. Psychiatry 57:343-350, 2005.

Carlezon Jr. et al., "Behavioral Effects of Citicoline (CDP-Choline) and Metabolites in Rats," Poster No. 67, Scottsdale, AR: Annual Meeting for the College on Problems of Drug Dependence, Jun. 18, 2001.

Castañé et al., "Lack of CB1 Cannabinoid Receptors Modifies Nicotine Behavioural Responses, But Not Nicotine Abstinence," Neuropharmacology 43:857-867, 2002.

Cohrs et al., "Sleep and Acetylcholine-Precursor-Substances," Pharmacopsychiatry 28:169, 1995. (Abstract).

Cyr et al., "Current Drug Therapy Recommendations for the Treatment of Attention Deficit Hyperactivity Disorder," Drugs 56:215-223, 1998.

Daly et al., "The Use of Tricyclic Antidepressants in Children and Adolescents," Pediatr. Clin. North Am. 45:1123-1135, 1998.

De Rosa et al., "Pharmacokinetics and Metabolism of Double-Labeled CDP Choline," Proceedings of the International Meeting on Novel Biochemical, Pharmacological and Clinical Aspects of Cytidinediphosphocholine, Sorrento, Italy, Jun. 12-14, 1984, pp. 139-157.

Elia, "Stimulants and Antidepressant Pharmacokinetics in Hyperactive Children," Psychopharmacol. Bull. 27:411-415, 1991.

Emslie et al., "Nontricyclic Antidepressants: Current Trends in Children and Adolescents," J. Am. Acad. Child Adolesc. Psychiatry 38:517-528, 1999.

English Translation of Official Action from the Patent Office of the Russian Federation for Application No. 2005122934/14 (issued Jun. 12, 2009).

Fioravanti et al., "Cytidinediphosphocholine (CDP Choline) for Cognitive and Behavioural Disturbances Associated with Chronic Cerebral Disorders in the Elderly," Cochrane Database Systems 2:CD000269 (2005).

Forester et al., "$^{31}$Phosphorus Magnetic Resonance Spectroscopy Study of Tissue Specific Changes in High Energy Phosphates Before and After Sertraline Treatment of Geriatric Depression," Int. J. Geriatr. Psychiatry 24:788-797, 2009.

Frey et al., "Myo-Inositol in Depressive and Healthy Subjects Determined by Frontal 1H-Magnetic Resonance Spectroscopy at 1.5 Tesla," J. Psychiatr. Res. 32:411-420, 1998.

Fux et al., "A Placebo-Controlled Cross Over Trial of Adjunctive EPA in OCD," J. Psychiatr. Res. 38:323-325, 2004.

G.-Coviella et al., "Effect of Cytidine(5')Diphosphocholine (CDP-Choline) on the Total Urinary Excretion of 3-Methoxy-4-Hydroxyphenylglycol (MHPG) by Rats and Humans," J. Neural Transm. 66:129-134, 1986.

G.-Coviella et al., "Enhancement by Cytidine of Membrane Phospholipid Synthesis," J. Neurochem. 59:338-343, 1992.

G.-Coviella et al., "Metabolism of Cytidine(5')-Diphosphocholine (CDP-Choline) Following Oral and Intravenous Administration to the Human and the Rat," Neurochem. Int. 11:293-297, 1987.

Geiger et al., "Cytidine and Uridine Requirement of the Brain," J. Neurochem. 1:93-100, 1956.

Giménez et al., "Changes in Brain Striatum Dopamine and Acetylcholine Receptors Induced by Chronic CDP-Choline Treatment of Aging Mice," Br. J. Pharmacol. 104:575-578, 1991.

Grau et al., "Study on the Protection of CDP-Choline Against Nicotine Intoxication," Arzneim.-Forsch. 33:1025-1026, 1983.

Greenberg, "Clinical Dimensions of Fatigue," Prim. Care Companion J. Clin. Psychiatry 4:90-93, 2002.

Hansen, "Blood Nucleoside and Nucleotide Studies in Mental Disease," Br. J. Psychiatry. 121:341-350, 1972.

HD Blog, "Triacetyluridine. Health Care & Huntington's Disease News," www.huntington.info, Dec. 3, 2003.

Higgins, "A Comparative Analysis of Antidepressants and Stimulants for the Treatment of Adults with Attention-Deficit Hyperactivity Disorder," J. Fam. Pract. 48:15-20, 1999.

Honda et al., "Sleep-Promoting Effects of Intraperitoneally Administered Uridine in Unrestrained Rats," Neurosci. Lett. 62:137-141, 1985.

Inoué et al., "Differential Sleep-Promoting Effects of Five Sleep Substances Nocturnally Infused in Unrestrained Rats," Proc. Natl Acad. Sci. U S A. 81:6240-6244, 1984.

Iosifescu et al., "Brain Bioenergetics and Response to Triiodothyronine Augmentation in Major Depressive Disorder," Biol. Psychiatry 63:1127-1134, 2008.

Jensen et al., "Triacetyluridine (TAU) Decreases Depressive Symptoms and Increases Brain pH in Bipolar Patients," Exp. Clin. Psychopharmacol. 16:199-206, 2008.

Karkishchenko et al., "Biosynthesis of Endogenous Pyrimidines in Anxiety and Depressive States of Different Etiologies," Zh. Nevropatol. Psikhiatr. Im. S. S. Korsakova (J. Neuropath. Psych.) 91:73-74, 1991.

Kaufman et al., "Cerebral Phosphorus Metabolite Abnormalities in Opiate-Dependent Polydrug Abusers in Methadone Maintenance," Psychiatry Res. 90:143-152, 1999.

Kennedy et al., "The Function of Cytidine Coenzymes in the Biosynthesis of Phospholipides," J. Biol. Chem. 222:193-214, 1956.

Kimura et al., "N3-Phenacyluridine, a Novel Hypnotic Compound, Interacts with the Benzodiazepine Receptor," Eur. J. Pharmacol. 311:265-269, 1996.

Kimura et al., "Possible Existence of a Novel Receptor for Uridine Analogues in the Central Nervous System Using Two Isomers, N3-(S)-(+)- and N3-(R)-(−)-Alpha-Hydroxy-Beta-Phenethyluridines," Biol. Pharm. Bull. 24:729-731, 2001.

Kimura et al., "Uridine Receptor: Discovery and Its Involvement in Sleep Mechanism," Sleep 24:251-260, 2001.

Konradi et al., "Molecular Evidence for Mitrochondrial Dysfunction in Bipolar Disorder," Arch. Gen. Psychiatry 61:300-308, 2004. Correction reprinted in Arch. Gen. Psychiatry 61:538, 2004.

Koob et al., "Drug Addiction, Dysregulation of Reward, and Allostasis," Neuropsychopharmacology 24:97-129, 2001.

Kouri et al., "Changes in Aggressive Behavior During Withdrawal from Long-Term Marijuana Use," Psychopharmacology 143:302-308, 1999.

Kozai et al., "Synthesis and Hypnotic Activities of 4-Thio Analogues of N3-Substituted Uridines," Chem. Pharm. Bull. (Tokyo) 49:1185-1188, 2001.

Krooth et al., "Effects of Natural Pyrimidines and of Certain Related Compounds on the Spontaneous Activity of the Mouse," J. Pharmacol. Exp. Ther. 207:504-514, 1978.

Levin et al., "Improved Regional Cerebral Blood Flow in Chronic Cocaine Polydrug Users Treated with Buprenorphine," J. Nucl. Med. 36:1211-1215, 1995.

Lyoo et al., "Frontal Lobe Gray Matter Density Decreases in Bipolar I Disorder," Biol. Psychiatry 55:648-651, 2004.

Lyoo et al., "Multinuclear Magnetic Resonance Spectroscopy of High-Energy Phosphate Metabolites in Human Brain Following Oral Supplementation of Creatine-Monohydrate," Psychiatry Res. 123:87-100, 2003.

Maldonado et al., "Involvement of the Endocannabinoid System in Drug Addiction," Trends Neurosci. 29:225-232, 2006. (pp. 1-8).

Marangell et al., "A Double-Blind, Placebo-Controlled Study of the Omega-3 Fatty Acid Docosahexaenoic Acid in the Treatment of Major Depression," Am. J. Psychiatry. 160:996-998, 2003.

Martin et al. "Omega-3 Polyunsaturated Fatty Acids Increase Purine but Not Pyrimidine Transport in L1210 Leukaemia Cells," Biochem. J. 315:329-333, 1996.

Martinet et al., "Effects of Cytidine-5'-Diphosphocholine on Norepinephrine, Dopamine, and Serotonin Synthesis in Various Regions of the Rat Brain," Arch. Int. Pharmacodyn. 239:52-61, 1979.

Martinet et al., "Interaction of CDP-Choline with Synaptosomal Transport of Biogenic Amines and Their Precursors in Vitro and in Vivo in the Rat Corpus Striatum," Experientia 34:1197-1199, 1978.

Mezinskis et al., "The Measurement of Craving," J. Addict. Dis. 20:67-85, 2001.

Monti et al., "Adenosine Analogues Modulate the Incidence of Sleep Apnea in Rats," Pharmacol. Biochem. Behav. 51:125-131, 1995.

Moore et al., "Lower Levels of Nucleoside Triphosphate in the Basal Ganglia of Depressed Subjects: A Phosphorous-31 Magnetic Resonance Spectroscopy Study," Am. J. Psychiatry 154:116-118, 1997.

National Institutes of Health, "Problem Sleepiness," NIH Publication No. 97/4071, pp. 1-4, Bethesda, MD, 1997.

Naydenov et al., "Differences in Lymphocyte Electron Transport Gene Expression Levels Between Subjects with Bipolar Disorder and Normal Controls in Response to Glucose Deprivation Stress," Arch. Gen. Psychiatry 64:555-564, E1-E7, 2007.

O'Leary et al., "Acute Marijuana Effects on rCBF and Cognition: A PET Study," Neuroreport 11:3835-3841, 2000.

Orsulak et al., "Antidepressant Drugs: Additional Clinical Uses," J. Fam. Pract. 28:209-216, 1989.

Pekkanen, "Your Inner Clock," Washingtonian 42:131-134, 2007.

Petkov et al., "Changes in the Brain Biogenic Monoamines Induced by the Nootropic Drugs Adafenoxate and Meclofenoxate and by Citicholine (Experiments on Rats)," Gen. Pharmacol. 21:71-75, 1990.

Petkov et al., "Effects of the Nootropic Agents Adafenoxate, Meclofenoxate and the Acetylcholine Precursor Citicholine on the Brain Muscarinic Receptors (Experiments on Rats)," Acta Physiol. Pharmacol. Bulg. 13:3-10, 1987.

Pokrovsky, "Encyclopedic Dictionary of Medical Terms," Meditsina Publishers (Moscow), pp, 97, 265, 2001.

Pugh et al., "Stedman's Medical Dictionary," Lippincott Williams & Wilkins, 27th Edition, Entry for "Insomnia," pp. 906-907, 2000.

Purdue News, "Deficiency in Omega-3 Fatty Acids Tied to ADHD in Boys," Jun. 1996.

Regenold et al., "Cerebrospinal Fluid Evidence of Increased Extra-Mitrochondrial Glucose Metabolism Implicates Mitochondrial Dysfunction in Multliple Sclerosis Disease Progression," J. Neurol. Sci. 275:106-112, 2008.

Regenold et al., "Elevated Cerebrospinal Fluid Lactate Concentrations in Patients with Bipolar Disorder and Schizophrenia: Implications for the Mitochondrial Dysfunction Hypothesis," Biol. Psychiatry 65:489-494, 2009.

Rejdak et al., "Citicoline Treatment Increases Retinal Dopamine Content in Rabbits," Ophthalmic Res. 34:146-149, 2002.

Renshaw et al., "Basal Ganglia Choline Levels in Depression and Response to Fluoxetine Treatment: An In Vivo Proton Magnetic Resonance Spectroscopy Study," Biol. Psychiatry 41:837-843, 1997.

Renshaw et al., "Multinuclear Magnetic Resonance Spectroscopy Studies of Brain Purines in Major Depression," Am. J. Psychiatry 158:2048-2055, 2001.

Repligen Press Release, "Repligen Reports Initial Clinical Data for Secretin in Schizophrenia: Follow-on Study Planned to Target a Cognitive Deficit of Schizophrenia," pp. 1-2, Feb. 4, 2005.

Repligen Press Release, "Repligen Reports Phase 1 Results of RG2133 in Bipolar Disorder and Depression: Additional Studies Planned with Uridine in Bipolar Disorder," pp. 1-2, Jun. 10, 2004.

Repligen Press Release, "Repligen Reports Phase 1 Results of RG2133 in Bipolar Disorder and Depression: Additional Studies Planned with Uridine in Bipolar Disorder," pp. 1-2, Jun. 9, 2004.

Repligen Press Release, "Repligen Reports Third Quarter 2001 Results: Company Updates Progress on Product Development Programs," pp. 1-2, Feb. 1, 2001.

Repligen Press Release, "Repligen's RG2417 Demonstrates Positive Activity in Preclinical Model of Anxiety: Data Presented at the Annual Meeting of Society for Neuroscience," pp. 1-2, Oct. 25, 2004.

Reply to Office Action and Declaration of Dr. James Rusche, submitted in U.S. Appl. No. 11/629,111 on Feb. 22, 2010.

Richardson et al., "Laterality Changes Accompanying Symptom Remission in Schizophrenia Following Treatment with Eicosapentaenoic Acid," Int. J. Psychophysiol. 34:333-339, 1999.

Roitman et al., "Creatine Monohydrate in Resistant Depression: A Preliminary Study," Biopolar. Disord. 9:754-758, 2007.

Romanov, "Sleep Medicine," Slovo Publishers (Moscow), p. 69, 1998.

Saligaut et al., "Capture de Dopamine Striatale Chez le Rat: Effects d'une Hypoxie Hypobare Agiüe et/ou d'un Traitement Oral Par la Cytidine Diphosphocholine" Circulation et Métabolisme du Cerveau 2:33-42, 1984. (English Abstract).

Saligaut et al., "Effects of Hypoxia and Cytidine (5') Diphosphocholine on the Concentrations of Dopamine, Norepinephrine and Metabolites in Rat Hypothalamus and Striatum," Arch. Int. Pharmacodyn. Ther. 285:25-33, 1987.

Schloesser et al., "Cellular Plasticity Cascades in the Pathophysiology and Treatment of Bipolar Disorder," Neuropsychopharmacology 33:110-133, 2008.

Sharpe, "CDP-Choline and Alpha-GPC: What to Feed Your Head," http://www.delano.com/ReferenceArticles/CDPc-aGPC-Sharpe.html, Feb. 15, 2006, pp. 1-6.

Shibuya et al., "Effects of CDP-Choline on Striatal Dopamine Levels and Behavior in Rats," Jpn. J. Pharmacol. 31:47-52, 1981.

Silveri et al., "Citicoline Enhances Frontal Lobe Bioenergetics as Measured by Phosphorus Magnetic Resonance Spectroscopy," NMR Biomed. 21:1066-1075, 2008.

Silveri et al., "Oral Citicoline Supplementation Significantly Alters Phosphorus Metabolites in the Anterior Cingulate Cortex," Program No. 301.2, Poster No. W16, 2007 Neuroscience Meeting Planner. San Diego, CA: Society for Neuroscience, Nov. 4, 2007.

Silveri et al., "S-Adenosyl-L-Methionine: Effects on Brain Bioenergetic Status and Transverse Relaxation Time in Healthy Subjects," Biol. Psychiatry 54:833-839, 2003.

Spielman et al., "Treatment of Chronic Insomnia by Restriction of Time in Bed," Sleep 10:45-56, 1987.

Stoll et al., "Omega 3 Fatty Acids in Bipolar Disorder: a Preliminary Double-Blind, Placebo-Controlled Trial," Arch. Gen. Psychiatry. 56:407-412, 1999.

Stork et al., "Mitochondrial Dysfunction in Bipolar Disorder: Evidence from Magnetic Resonance Spectroscopy Research," Mol. Psychiatry 10:900-919, 2005.

Stradomskii et al., "Pyrimidine Metabolism in Depression Anxiety Disorders," Izvestiya Severo-Kavkazskogo Nauchnogo Tsentra Vysshei Shkoly Estestvennye Nauki 1:106-110, 1990. (Abstract).

Sun et al. "Observation of Therapeutic Effects of High Dose Citicoline on the Emergency Treatment of 100 Cases of Hypnotics Poisoning," China Pharmacist 2:77-78, 1999. (English Translation (3 pages)).

Tanskanen et al., "Fish Consumption and Depressive Symptoms in the General Population in Finland," Psychiatr. Serv. 52:529-531, 2001.

Teicher et al., "Functional Deficits in Basal Ganglia of Children with Attention-Deficit/Hyperactivity Disorder Shown with Functional Magnetic Resonance Imaging Relaxometry," Nat. Med. 6:470-473, 2000.

Trovarelli et al., "The Influence of Cytidine on the Endogenous Pool of CDP-Choline, CDP-Ethanolamine, and CMP of the Rat Brain," Neurochem. Res. 9:73-79, 1984.

van Groeningen et al., "Clinical and Pharmacokinetic Studies of Prolonged Administration of High-Dose Uridine Intended for Rescue from 5-FU Toxicity," Cancer Treat. Rep. 70:745-750, 1986.

van Groeningen et al., "Clinical and Pharmacologic Study of Orally Administered Uridine," J. Natl. Cancer Inst. 83:437-441, 1991.

Virtue, "Nutrition as Attention Deficit Disorder ADHD Alternative Treatment: Help is as Close as the Kitchen," www.naturalhealthweb.com, 1999. (pp. 1-4).

Wilson, "Increasing Serotonin Crucial for Treating Obsessive-Compulsive Disorder: Presented at SFN," Doctor's Guide Personal Edition, pp. 1-2, Nov. 14, 2003.

Wurtman et al., "Synapse Formation is Enhanced by Oral Administration of Uridine and DHA, the Circulating Precursors of Brain Phosphatides," J. Nutr. Health Aging 13:189-197, 2009.

Wurtman et al., "Synaptic Proteins and Phospholipids are Increased in Gerbil Brain by Administering Uridine Plus Docosahexaenoic Acid Orally," Brain Res. 1088:83-92, 2006.

Yoon et al., "Decreased Glutamate/Glutamine Levels May Mediate Cytidine's Efficacy in Treating Bipolar Depression: A Longitudinal Proton Magnetic Resonance Spectroscopy Study," Neurophyschopharmacology 34:1810-1818, 2009.

Zaharov et al., "Cognitive Disorders in Neurology Practice," A Difficult Patient No. 5, 2005. [Available at http://www.t-pacient.ru/archive/n5-2005/n5-2005__23.html] (pp. 1-5).

Zhao et al., "Effects of Uridine in Models of Epileptogenesis and Seizures," Epilepsy Res. 70:73-82, 2006.

Zhao et al., "Effects of Uridine on Kindling," Epilepsy Behav. 13:47-51, 2008.

Alvarez et al., "Double-Blind Placebo-Controlled Study with Citicoline in APOE Genotyped Alzheimer's Disease Patients. Effects on Cognitive Performance, Brain Bioelectrical Activity and Cerebral Perfusion," *Methods Find Exp. Clin. Pharmacol.* (Abstract) 21:633-644 (1999).

Fernandez, "Efficacy and Safety of Oral CDP-Choline: Drug Surveillance Study in 2817 Cases," *Arzneimittelforschung. Drug Res.* 33:1073-1080 (1983).

Fioravanti et al., "Cytidinediphosphocholine (CDP Choline) for Cognitive and Behavioural Disturbances Associated with Chronic Cerebral Disorders in the Elderly," *Cochrane Database Systems* (Abstract) 2:CD000269 (2000).

Greenwell, "Enhancing Cognitive Function: Keeping Your Memory in Tip Top Shape," *LE (Life Extension) Magazine* (2000). [Available at www.lef.org/magazine/mag2000/may00-cover.html.].

Katzung, "Basic & Clinical Pharmacology," *Appleton & Lang*, Seventh Edition 62:521-523 (1998).

Radulovacki, "Adenosine Analogs and Sleep in Rats," J. Pharmacol. Exper. Ther. 228:268-274 (1984).

Satoh et al., "Involvement of Adenosine $A_{2A}$ Receptor in Sleep Promotion," *Euro. J. Pharmacol.* 351:155-162 (1998).

Scammell at al., "An Adenosine A2a Agonist Increases Sleep and Induces Fos in Ventrolateral Preoptic Neurons," *Neurosci.* 107:653-663 (2001).

Shargel et al., "Comprehensive Pharmacy Review," *Lippincott Williams & Wilkins*, Fourth Edition 547-548 (2001).

\* cited by examiner

COMPOUNDS FOR THE TREATMENT OF PSYCHIATRIC OR SUBSTANCE ABUSE DISORDERS

CROSS-REFERENCE TO RELATED APPLICATIONS

This application is a divisional of co-pending U.S. application Ser. No. 09/810,109, filed Mar. 15, 2001, which claims benefit of U.S. Provisional Application Nos. 60/189,727, 60/189,811, and 60/189,728, all filed Mar. 16, 2000, each of which is hereby incorporated by reference.

STATEMENT AS TO FEDERALLY SPONSORED RESEARCH

This invention was funded, in part, by grants DA09448 and DA11321, from the National Institute on Drug Abuse, and MH-48343 and MH-53636 from the National Institute of Mental Health. The government may have certain rights in the invention.

BACKGROUND OF THE INVENTION

This invention relates to methods for the treatment of psychiatric or substance abuse disorders.

Psychiatric and substance abuse disorders present unique complications for patients, clinicians, and care givers. These disorders are difficult to diagnose unequivocally and fear of societal condemnation, as well as lack of simple and effective therapies, often results in patients who are reluctant to disclose their symptoms to health professionals, leading to adverse societal and health consequences.

Psychiatric and substance abuse disorders include alcohol and opiate abuse or dependence, depression, dysthymia, and attention-deficit hyperactivity disorder, among others, and occur in people of all ages and backgrounds.

Use of substances such as alcohol and opiates often leads to addiction and dependence on these substances, causing a variety of adverse consequences, including clinical toxicity, tissue damage, physical dependence and withdrawal symptoms, and an impaired ability to maintain social and professional relationships. The etiology of substance abuse or dependence is unknown, although factors such as the user's physical characteristics (e.g., genetic predisposition, age, weight), personality, or socioeconomic class have been postulated to be determinants.

Depression and dysthymia are prevalent disorders that are often chronic and associated with frequent relapses and long duration of episodes. These disorders include psychosocial and physical impairment and a high suicide rate among those affected. A lifetime prevalence of approximately 17% has been widely reported, and the likelihood of recurrence is more than 50% (Angst, J. Clin. Psychiatry 60 Suppl. 6:5-9, 1999). The neurological mechanisms underlying depression and dysthymia are poorly understood, with a concomitant lack in suitable pharmacological therapies for the treatment of these disorders. Current therapies often have many adverse effects and are not suitable for administration to certain cohorts. For example, depression in the elderly, particularly in those in long-term care facilities, is common and is often more refractory to treatment than depression in young or middle-aged adults; however, the elderly are particularly sensitive to the common adverse effects of many antidepressant drugs, particularly the anticholinergic side effects. Similarly, therapies that are suitable for administration to adults may not be suitable for children.

Attention-deficit hyperactivity disorder (ADHD) is a highly heritable and prevalent neuropsychiatric disorder estimated to affect 6% of the school-age children in the United States. ADHD typically occurs in early childhood and persists into adulthood, but is often not diagnosed until or after adolescence. Clinical hallmarks of ADHD are inattention, hyperactivity, and impulsivity, which often respond to treatment with stimulants (e.g., methylphenidate, dextroamphetamine, or magnesium pemoline), although non-stimulant drugs such as beta-blockers (e.g., propranolol or nadolol), tricyclic antidepressants (e.g., desipramine), and anti-hypertensives (e.g., clonidine) are also used. Treatment with these drugs, however, is complicated by adverse effects, including the possibility of abuse of the medication, growth retardation, disturbance of heart rhythms, elevated blood pressure, drowsiness, depression, sleep disturbances, headache, stomachache, appetite suppression, rebound reactions, and by the unclear long-term effects of drug administration on brain function.

Simple and effective pharmacological treatments for these disorders have proven scarce to date. It would be beneficial to provide pharmacotherapies suitable for administration to all populations, including the elderly and children, for the treatment of substance abuse and psychiatric disorders.

SUMMARY OF THE INVENTION

In general, the invention features methods of treating substance abuse or psychiatric disorders, for example, alcohol or opiate abuse or dependency, unipolar depression or dysthymia, or attention-deficit hyperactivity disorder, by administering a therapeutically-effective amount of a cytidine-containing, cytosine-containing, creatine-containing, uridine-containing, adenosine-containing, or adenosine-elevating compound to a mammal. Any of the cytidine-containing, cytosine-containing, creatine-containing, uridine-containing, adenosine-containing, or adenosine-elevating compounds of the invention may be administered separately.

In preferred embodiments, the cytidine-containing compound is cytidine, CDP, or CDP-choline; the cytidine-containing compound includes choline; and the mammal is a human child, adolescent, adult, or older adult. In other preferred embodiments, the CDP-choline is administered orally and the administration is chronic.

In other preferred embodiments, a brain phospholipid (e.g., lecithin) or a brain phospholipid precursor (e.g., a fatty acid or a lipid), is also administered to the mammal. In other preferred embodiments, an antidepressant is also administered to the mammal.

In other preferred embodiments, the mammal has a co-morbid neurological disease, for example, post-stroke depression.

As used herein, by "alcohol" is meant a substance containing ethyl alcohol.

By "opiate" is meant any preparation or derivative of opium, which is a naturally occurring substance extracted from the seed pod of a poppy plant (e.g., *Papaver somniferum*) and which contains at least one of a number of alkaloids including morphine, noscapine, codeine, papaverine, or thebaine. Heroin, an illegal, highly addictive drug is processed from morphine. For the purposes of this invention, the term opiate includes opioids.

By "opioid" is meant a synthetic narcotic that resembles an opiate in action, but is not derived from opium.

By "abuse" is meant excessive use of a substance, particularly one that may modify body functions, such as alcohol or opiates.

By "dependency" is meant any form of behavior that indicates an altered or reduced ability to make decisions resulting, at least in part, from the use of alcohol or opiates. Representative forms of dependency behavior may take the form of antisocial, inappropriate, or illegal behavior and include those behaviors directed at the desire, planning, acquiring, and use of alcohol or opiates. This term also includes the psychic craving for alcohol or an opiate that may or may not be accompanied by a physiological dependency, as well as a state in which there is a compulsion to take alcohol or an opiate, either continuously or periodically, in order to experience its psychic effects or to avoid the discomfort of its absence. Forms of "dependency" include habituation, that is, an emotional or psychological dependence on alcohol or an opiate to obtain relief from tension and emotional discomfort; tolerance, that is, the progressive need for increasing doses to achieve and sustain a desired effect; addiction, that is, physical or physiological dependence which is beyond voluntary control; and use of alcohol or an opiate to prevent withdrawal symptoms. Dependency may be influenced by a number of factors, including physical characteristics of the user (e.g., genetic predisposition, age, gender, or weight), personality, or socioeconomic class.

By "dysthymia" or "dysthymic disorder" is meant a chronically depressed mood that occurs for most of the day, more days than not, for at least two years. In children and adolescents, the mood may be irritable rather than depressed, and the required minimum duration is one year. During the two year period (one year for children or adolescents), any symptom-free intervals last no longer than 2 months. During periods of depressed mood, at least two of the following additional symptoms are present: poor appetite or overeating, insomnia or hypersomnia, low energy or fatigue, low self-esteem, poor concentration or difficulty making decisions, and feelings of hopelessness. The symptoms cause clinically significant distress or impairment in social, occupational (or academic), or other important areas of functioning. The diagnosis of dysthymia is not made if: the individual has ever had a manic episode, a mixed episode, a hypomanic episode; has ever met the criteria for a cyclothymic disorder; the depressive symptoms occur exclusively during the course of a chronic psychotic disorder (e.g., schizophrenia); or if the disturbance is due to the direct physiological effects of a substance or a general medical condition. After the initial two-years of dysthymic disorder, major depressive episodes may be superimposed on the dysthymic disorder ("double depression"). (Diagnostic and Statistical Manual of Mental Disorders (DSM IV), American Psychiatric Press, $4^{th}$ Edition, 1994).

By "unipolar depression" or "major depressive disorder" is meant a clinical course that is characterized by one or more major depressive episodes in an individual without a history of manic, mixed, or hypomanic episodes. The diagnosis of unipolar depression is not made if: manic, mixed, or hypomanic episodes develop during the course of depression; if the depression is due to the direct physiological effects of a substance; if the depression is due to the direct physiological effects of a general medical condition; if the depression is due to a bereavement or other significant loss ("reactive depression"); or if the episodes are better accounted for by schizoaffective disorder and are not superimposed on schizophrenia, schizophreniform disorder, delusional disorder, or psychotic disorder. If manic, mixed, or hypomanic episodes develop, then the diagnosis is changed to a bipolar disorder. Depression may be associated with chronic general medical conditions (e.g., diabetes, myocardial infarction, carcinoma, stroke). Generally, unipolar depression is more severe than dysthymia.

The essential feature of a major depressive episode is a period of at least two weeks during which there is either depressed mood or loss of interest or pleasure in nearly all activities. In children and adolescents, the mood may be irritable rather than sad. The episode may be a single episode or may be recurrent. The individual also experiences at least four additional symptoms drawn from a list that includes changes in appetite or weight, sleep, and psychomotor activity; decreased energy; feelings of worthlessness or guilt; difficulty thinking, concentrating, or making decisions; or recurrent thoughts of death or suicidal ideation, plans, or attempts. Each symptom must be newly present or must have clearly worsened compared with the person's preepisode status. The symptoms must persist for most of the day, nearly every day, for at least two consecutive weeks, and the episode must be accompanied by clinically significant distress or impairment in social, occupational (or academic), or other important areas of functioning. (Diagnostic and Statistical Manual of Mental Disorders (DSM IV), American Psychiatric Press, $4^{th}$ Edition, 1994).

By "neurological disease" is meant a disease, which involves the neuronal cells of the nervous system. Specifically included are prion diseases (e.g., Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, tyrosinemia, and fragile X syndrome); pathologies of the mature brain (e.g., neurofibromatosis, Huntington's disease, depression, amyotrophic lateral sclerosis, multiple sclerosis); conditions that strike in adulthood (e.g. Alzheimer's disease, Creutzfeldt-Jakob disease, Lewy body disease, Parkinson's disease, Pick's disease); and other pathologies of the brain (e.g., brain mishaps, brain injury, coma, infections by various agents, dietary deficiencies, stroke, multiple infarct dementia, and cardiovascular accidents). By "co-morbid" or "comorbidity" is meant a concomitant but unrelated pathology, disease, or disorder. The term co-morbid usually indicates the coexistence of two or more disease processes.

By "attention-deficit hyperactivity disorder" or "ADHD" is meant a behavioral disorder characterized by a persistent and frequent pattern of developmentally inappropriate inattention, impulsivity, and hyperactivity. Indications of ADHD include lack of motor coordination, perceptual-motor dysfunctions, EEG abnormalities, emotional lability, opposition, anxiety, aggressiveness, low frustration tolerance, poor social skills and peer relationships, sleep disturbances, dysphoria, and mood swings ("Attention Deficit Disorder," The Merck Manual of Diagnosis and Therapy ($17^{th}$ Ed.), eds. M. H. Beers and R. Berkow, Eds., 1999, Whitehouse Station, N.J.).

By "treating" is meant the medical management of a patient with the intent that a cure, amelioration, or prevention of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; preventive treatment, that is, treatment directed to prevention of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

By "therapeutically-effective amount" is meant an amount of a cytidine-containing, cytosine-containing compound, a uridine-containing compound, a creatine-containing compound, an adenosine-containing compound, and an adenosine-elevating compound sufficient to produce a healing, curative, prophylactic, stabilizing, or ameliorative effect in the treatment of attention-deficit hyperactive disorder, unipolar depression, dysthymia, alcohol abuse, alcohol dependency, opiate abuse, or opiate dependency.

By "cytidine-containing compound" is meant any compound that includes, as a component, cytidine, CMP, CDP, CTP, dCMP, dCDP, or dCTP. Cytidine-containing compounds can include analogs of cytidine. Preferred cytidine-containing compounds include, without limitation, CDP-choline and cytidine 5'-diphosphocholine, frequently prepared as cytidine 5'-diphosphocholine [sodium salt] and also known as citicoline.

By "cytosine-containing compound" is meant any compound that includes, as a component, cytosine. Cytosine-containing compounds can include analogs of cytosine.

By "adenosine-containing compound" is meant any compound that includes, as a component, adenosine. Adenosine-containing compounds can include analogs of adenosine.

By "adenosine-elevating compound" is meant any compound that elevates brain adenosine levels, for example, compounds which inhibit or alter adenosine transport or metabolism (e.g., dipyridamole or S-adenosylmethionine).

By "uridine-containing compound" is meant any compound that includes as a component, uridine or UTP. Uridine-containing compounds can include analogs of uridine, for example, triacetyl uridine.

By "creatine-containing compound" is meant any compound that includes as a component, creatine. Creatine-containing compounds can include analogs of creatine.

By "phospholipid" is meant a lipid containing phosphorus, e.g., phosphatidic acids (e.g., lecithin), phosphoglycerides, sphingomyelin, and plasmalogens. By "phospholipid precursor" is meant a substance that is built into a phospholipid during synthesis of the phospholipid, e.g., fatty acids, glycerol, or sphingosine.

By "child or adolescent" is meant an individual who has not attained complete growth and maturity. Generally, a child or adolescent is under twenty-one years of age.

By "older adult" is meant an individual who is in the later stage of life. Generally, an older adult is over sixty years of age.

The present invention provides therapeutics for the treatment of substance abuse or dependencies, unipolar depression or dysthymia, and ADHD. The compounds utilized herein are relatively non-toxic, and CDP-choline, uridine, and triacetyl uridine, in particular, are pharmocokinetically understood and known to be well tolerated by mammals. The present invention, therefore, provides treatments that are likely to have few adverse effects and may be administered to children and adolescents, as well as the elderly, or those whose health is compromised due to existing physical conditions.

DETAILED DESCRIPTION OF THE INVENTION

Figure 1:
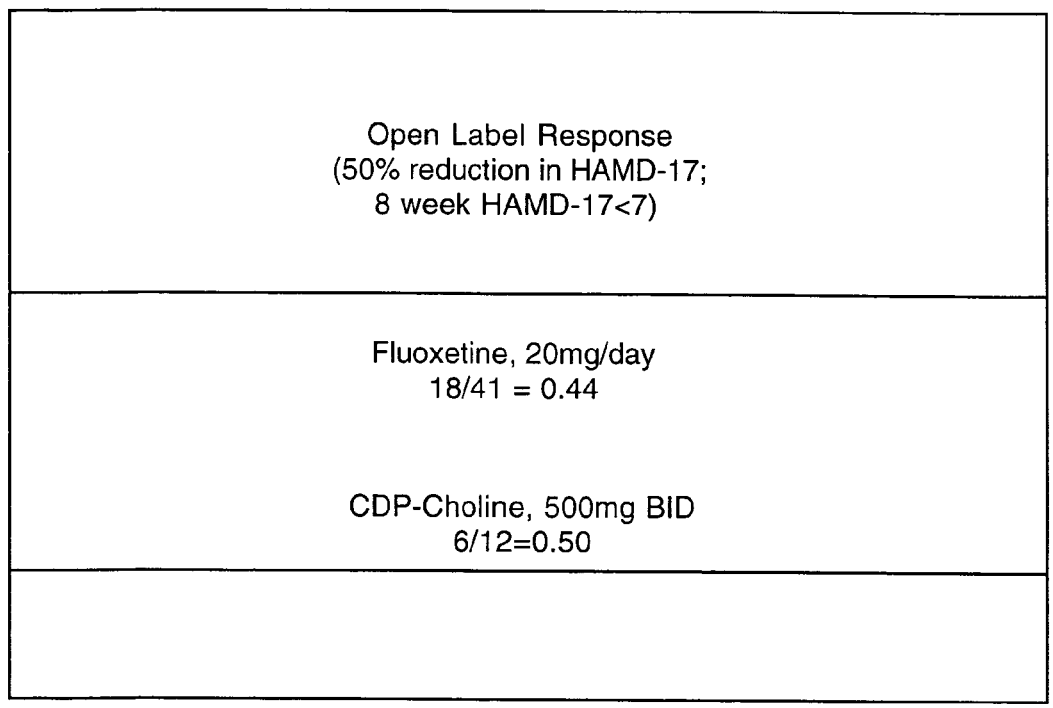
FIG. 1 is a bar graph showing the relative efficacies of CDP-choline and fluoxetine.
Figure 1:
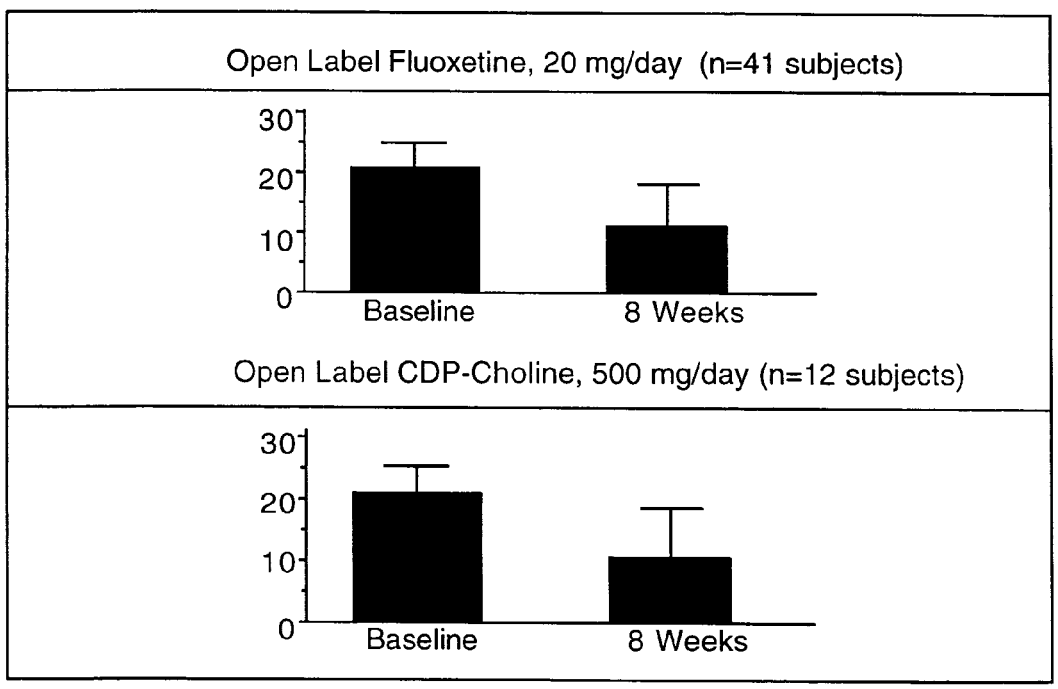

The invention described herein features methods for the treatment of psychiatric or substance abuse disorders such as alcohol and opiate abuse or dependence, unipolar depression, dysthymia, attention-deficit hyperactivity disorder (ADHD), and their symptoms.

To this end, the invention features the use of cytidine-containing, cytosine-containing, uridine-containing, creatine-containing, adenosine-containing, and adenosine-elevating compounds to alleviate symptoms of these disorders. A preferred cytidine-containing compound is CDP-choline (also referred to as citicoline or CDP choline [sodium salt]), a preferred adenosine-containing compound is S-adenosylmethionine (SAMe), and a preferred uridine-containing compound is triacetyl uridine.

The cytidine-containing, cytosine-containing, uridine-containing, creatine-containing, adenosine-containing, or adenosine-elevating compounds may be co-administered with other compounds that are precursors for the synthesis of brain phospholipids, e.g., fatty acids, lipids, or lecithin.

Unipolar Depression or Dysthymia

The invention provides original data regarding the efficacy of CDP-choline in human trials and demonstrates that cytidine-containing and cytosine-containing compounds can be used to treat depression. CDP-choline has been found to have two important new therapeutic properties. First, CDP-choline improves brain chemistry, e.g., increases phospholipid synthesis, in healthy adults. This effect is particularly apparent in older adults. Second, CDP-choline has antidepressant effects that are similar to those of fluoxetine, a widely-used drug for the treatment of depression.

Cytidine-containing and cytosine-containing compounds are particularly efficacious in treating the elderly, and these compounds are efficacious in treating depression in patients with a co-morbid neurological disease (e.g., post-stroke depression). In addition, these compounds may be administered in conjunction with, and thereby work synergistically with, phospholipids (e.g., lecithin) or compounds that are precursors for the synthesis of brain phospholipids (e.g., fatty acids or lipids).

Alcohol or Opiate Abuse or Dependence

Phosphorus-31 magnetic resonance spectroscopy (MRS) studies indicate that persons who are dependent upon alcohol and opiates have decreased brain levels of phospholipids. In addition, data derived from healthy older persons, indicates that chronic administration of CDP-choline is associated with neurochemical changes consistent with phospholipid synthesis. Increasing brain levels of cytosolic adenosine also provides effective therapy for alcohol or opiate abuse or dependency, because energy in the form of ATP is required to support phospholipid synthesis.

Attention Deficit Hyperactivity Disorder (ADHD)

Functional magnetic resonance imaging (fMRI) experiments in children diagnosed with ADHD indicate that symptoms of hyperactivity and inattention are strongly correlated with measures of blood flow within the putamen nuclei, which are strongly dopaminergic brain regions. In addition, administration of methylphenidate, a stimulant used to treat ADHD, increases blood flow in the putamen in parallel with a decrease in motor activity. ADHD symptoms may be closely tied to functional abnormalities in the putamen, which is predominantly involved in the regulation of motoric behavior. Accordingly, because cytidine-containing and cytosine-containing compounds (e.g., CDP-choline) have dopaminergic activity, these compounds may be used to treat persons diagnosed with ADHD without many of the side effects associated with stimulant therapies. In particular, treatments with cytidine-containing or cytosine-containing compounds are effective in treating hyperactivity in children diagnosed with ADHD.

Cytidine-Containing and Cytosine-Containing Compounds

Useful cytidine-containing or cytosine-containing compounds may include any compound comprising one of the following: cytosine, cytidine, CMP, CDP, CTP, dCMP, dCDP, and dCTP. Preferred cytidine-containing compounds include CDP-choline and cytidine 5'-diphosphocholine [sodium salt]. This list of cytidine-containing and cytosine-containing compounds is provided to illustrate, rather than to limit the invention, and the compounds described above are commercially available, for example, from Sigma Chemical Company (St. Louis, Mo.).

Figure 5:
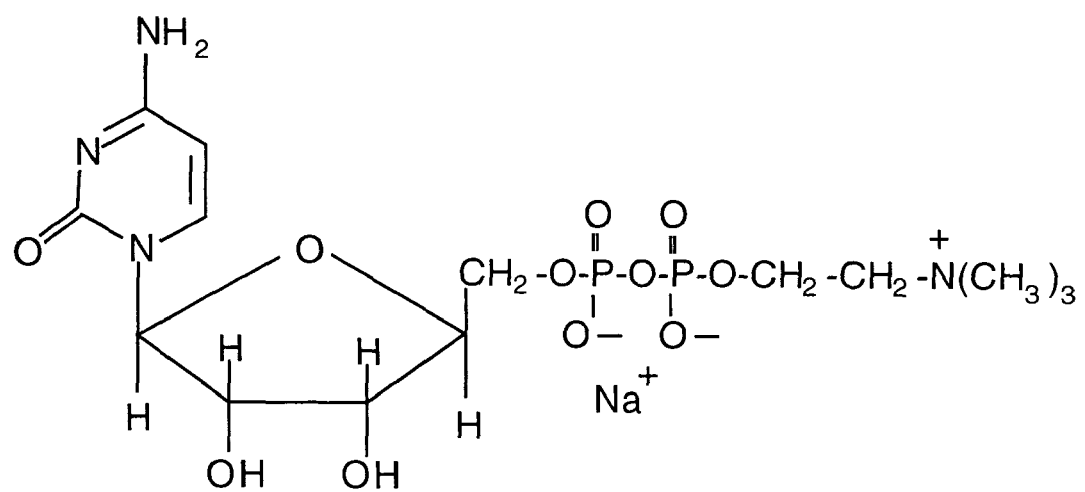
FIG. 5 is a schematic illustration of the molecular structure of CDP-choline.

CDP-choline is a naturally occurring compound that is hydrolyzed into its components of cytidine and choline in vivo. CDP-choline is synthesized from cytidine-5'-triphosphate and phosphocholine with accompanying production of inorganic pyrophosphate in a reversible reaction catalyzed by the enzyme CTP:phosphocholine cytidylyltransferase (Weiss, Life Sciences 56:637-660, 1995). CDP-choline is available for oral administration in a 500 mg oblong tablet. Each tablet contains 522.5 mg CDP-choline sodium, equivalent to 500 mg of CDP-choline. Matching placebo tablets are also available. The excipients contained in both active and placebo tablets are talc, magnesium stearate, colloidal silicon dioxide, hydrogenated castor oil, sodium carboxy-methylcellulose, and microcrystalline cellulose. The molecular structure of CDP-choline [sodium salt] is provided in FIG. 5.

Other formulations for treatment or prevention of psychiatric and substance abuse disorders may take the form of a cytosine-containing or cytidine-containing compound combined with a pharmaceutically-acceptable diluent, carrier, stabilizer, or excipient.

Adenosine-Containing and Adenosine-Elevating Compounds

Adenosine-containing or adenosine-elevating compounds provide useful therapies because these compounds provide the ATP needed for phospholipid synthesis. Useful adenosine-containing or adenosine-elevating compounds include, without limitation, any compound comprising one of the following adenosine, ATP, ADP, or AMP. One preferred adenosine-containing compound is S-adenosylmethionine (SAMe).

In addition, compounds are known that are capable of increasing adenosine levels by other mechanisms. For example, adenosine uptake can be inhibited by a number of known compounds, including propentofylline (described in U.S. Pat. No. 5,919,789, hereby incorporated by reference). Another known compound that inhibits adenosine uptake is EHNA.

Other useful compounds that can be used to increase brain adenosine levels are those that inhibit enzymes that break down adenosine, (e.g., adenosine deaminase and adenosine kinase). Finally, administering compounds that contain adenosine or precursors of adenosine, which are released as adenosine in vivo, can also be used.

Uridine-Containing Compounds

Uridine and uridine-containing compounds provide useful therapies because these compounds can be converted to CTP, a rate-limiting factor in PC biosynthesis (Wurtman et al., Biochemical Pharmacology 60:989-992, 2000). Useful uridine-containing compounds include, without limitation, any compound comprising uridine, UTP, UDP, or UMP. A preferred uridine-containing compound is triacetyl uridine. Uridine and uridine-containing compounds and analogs are well tolerated in humans.

Creatine-Containing Compounds

Creatine and creatine-containing compounds provide useful therapies because these compounds, by virtue of increasing brain phospholipid levels, can raise the levels of ATP. Creatine and creatine-containing compounds are known to be well tolerated at relatively high doses in humans.

Administration

Conventional pharmaceutical practice is employed to provide suitable formulations or compositions for administration to patients. Oral administration is preferred, but any other appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for intravenous administration); for oral administration, formulations may be in the form of liquids, tablets, or capsules; and for intranasal formulations, in the form of powders, nasal drops, or aerosols.

Methods well known in the art for making formulations are described, for example, in "Remington: The Science and Practice of Pharmacy" (19th ed.) ed. A. R. Gennaro, 1995, Mack Publishing Company, Easton, Pa. Formulations for parenteral administration may, for example, contain excipients, sterile water, saline, polyalkylene glycols such as polyethylene glycol, oils of vegetable origin, or hydrogenated naphthalenes.

If desired, slow release or extended release delivery systems may be utilized. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Preferably, the compounds of the invention, such as CDP-choline, are administered at a dosage of at least 500 mg twice daily by oral administration. Orally administered CDP-choline is bioavailable, with more than 99% of CDP-choline and/or its metabolites absorbed and less than 1% excreted in feces. CDP-choline, administered either orally or intravenously, is rapidly converted into the two major circulating metabolites, choline and cytidine. Major excretion routes are lung (12.9%) and urine (2.4%); the rest of the dose (83.9%) is apparently metabolized and retained in tissues.

In general, the compounds of the invention, such as CDP-choline, uridine, UTP, creatine, or SAMe, are administered at a dosage appropriate to the effect to be achieved and are typically administered in unit dosage form. The dosage preferably ranges from 50 mg per day to 2000 mg per day. The exact dosage of the compound may be dependent, for example, upon the age and weight of the recipient, the route of administration, and the severity and nature of the symptoms to be treated. In general, the dosage selected should be sufficient to prevent, ameliorate, or treat alcohol or opiate abuse or dependency, or one or more symptoms thereof, without producing significant toxic or undesirable side effects. As noted above, the preferred route of administration for most indications is oral.

In the case of CDP-choline, there have been no reported cases of overdoses. CDP-choline toxicity is largely self-limiting, ingestion of large amounts in preclinical studies shows common cholinergic symptoms (salivation, lacrimation, urination, defecation, and vomiting).

Combination with Other Therapeutics

The cytidine-containing, cytosine-containing, uridine-containing, creatine-containing, adenosine-containing, and adenosine-elevating compounds of the invention may be administered as a monotherapy, in combination with each other, or in combination with other compounds for the treatment of psychiatric and substance abuse disorders, including compounds for the treatment of alcohol or opiate abuse or dependency, or other physiological or psychological conditions associated with alcohol or opiate abuse or dependency, unipolar depression and dysthymia, and ADHD.

Preferably, the compounds of the invention, may be administered in conjunction with lower doses of current treatments for these disorders, including stimulants and antidepressants. For example, the compounds of the invention may be administered with phospholipids, e.g., lecithin, or with brain phospholipid precursors, e.g., fatty acids or lipids, or may be administered as an adjunct to standard therapy for the treatment of psychiatric or substance abuse disorders.

In one particular example, the compound of the invention may be administered in combination with an antidepressant, anticonvulsant, antianxiety, antimanic, antipyschotic, antiobsessional, sedative-hypnotic, stimulant, or antihypertensive medication. Examples of these medications include, but are not limited to, the antianxiety medications, alprazolam, buspirone hydrochloride, chlordiazepoxide, chlordiazepoxide hydrochloride, clorazepate dipotassium, desipramine hydrochloride, diazepam, halazepam, hydroxyzine hydrochloride, hydroxyzine pamoate, lorazepam, meprobamate, oxazepam, prazepam, prochlorperazine maleate, prochlorperazine, prochlorperazine edisylate, and trimipramine maleate; the anticonvulsants, amobarbital, amobarbital sodium, carbamazepine, chlordiazepoxide, chlordiazepoxide hydrochloride, clorazepate dipotassium, diazepam, divalproex sodium, ethosuximide, ethotoin, gabapentin, lamotrigine, magnesium sulfate, mephenytoin, mephobarbital, methsuximide, paramethadione, pentobarbital sodium, phenacemide, phenobarbital, phenobarbital sodium, phensuximide, phenytoin, phenytoin sodium, primidone, secobarbital sodium, trimethadione, valproic acid, and clonazepam; the antidepressants, amitriptyline hydrochloride, amoxapine, bupropion hydrochloride, clomipramine hydrochloride, desipramine hydrochloride, doxepin hydrochloride, fluoxetine, fluvoxamine, imipramine hydrochloride, imipramine pamoate, isocarboxazid, lamotrigine, maprotoline hydrochloride, nortriptyline hydrochloride, paroxetine hydrochloride, phenelzine sulfate, protriptyline hydrochloride, sertraline hydrochloride, tranylcypromine sulfate, trazodone hydrochloride, trimipramine maleate, and venlafaxine hydrochloride; the antimanic medications, lithium carbonate and lithium citrate; the antiobsessional medications, fluvoxamine, and clomipramine hydrochloride; the antipsychotic medications, acetophenazine maleate, chlorpromazine hydrochloride, chlorprothixene, chlorprothixene hydrochloride, clozapine, fluphenazine decanoate, fluphenazine enathrate, fluphenazine hydrochloride, haloperidol decanoate, haloperidol, haloperidol lactate, lithium carbonate, lithium citrate, loxapine hydrochloride, loxapine succinate, mesoridazine besylate, molindone hydrochloride, perphenazine, pimozide, prochlorperazine maleate, prochlorperazine, prochlorperazine edisylate, promazine hydrochloride, risperidone, thioridazine, thioridazine hydrochloride, thiothixene, thiothixene hydrochloride, and trifluoperzine hydrochloride; the sedative-hypnotic medications, amobarbital, amobarbital sodium, aprobarbital, butabarbital, chloral hydrate, chlordiazepoxide, chlordiazepoxide hydrochloride, clorazepate dipotassium, diazepam, diphenhydramine, estazolam, ethchlorvynol, flurazepam hydrochloride, glutethimide, hydroxyzine hydrochloride, hydroxyzine pamoate, lorazepam, methotrimeprazine hydrochloride, midazolam hydrochloride, non prescription, oxazepam, pentobarbital sodium, phenobarbital, phenobarbital sodium, quazepam, secobarbital sodium, temazepam, triazolam, and zolpidem tartrate; the stimulants, dextroamphetamine sulfate, methamphetamine hydrochloride, methylphenidate hydrochloride, and pemoline; and the antihypertensive, clonidine.

The following examples are provided for the purpose of illustrating the invention and should not be construed as limiting.

EXAMPLES

Unipolar Depression or Dysthymia

Treatment of Human Subjects with Cytidine- or Cytosine-Containing Compounds

Proton and phosphorus magnetic resonance (MR) spectroscopy studies of subjects with mood disorders have characterized two patterns of altered neurochemistry associated with depression. The first pattern indicates a change (increase or decrease) in cytosolic choline, as well as increased frontal lobe phosphomonoesters, while the second pattern points to decreased brain purines (cytosolic adenosine- and cytidine-containing compounds) and decreased nucleoside triphosphates (NTP). The former results reflect altered phospholipid metabolism, while the latter results indicate changes in cerebral energetics. Although few longitudinal studies have been conducted, these altered metabolite levels appear to be mood state, rather than trait, dependent.

To assess whether chronic CDP-choline administration leads to detectable changes in lipid metabolite resonances in phosphorus-31 MR spectra, eighteen healthy subjects (mean age: 70) were administered 500 mg of an oral formulation of CDP-choline daily for a six week period. From weeks 6 to 12, half of the subjects continued to receive CDP-choline and half received placebo in a double-blind fashion. The MR data demonstrated that CDP-choline treatment was associated with a significant increase in brain phosphodiesters ($p=0.008$), a finding that is indicative of increased phospholipid synthesis. Neuropsychological testing also revealed increases in verbal fluency ($p=0.07$), verbal learning ($p=0.003$), visuospatial learning ($p=0.0001$) across all subjects at week twelve. CDP-choline administration, therefore, improves measures of verbal fluency and spatial memory in healthy adults and results in increased brain phospholipid synthesis in older adults, particularly during chronic administration.

In a second study, twelve depressed subjects (mean age 40) received 500 mg of an oral formulation of CDP-choline twice daily for eight weeks. With eight weeks of treatment, mean 17-item Hamilton Depression Rating Scale (HDRS) scores decreased from 21±3 to 10±7 ($p<0.0001$). A successful response to CDP-choline was also associated with a reduction in the proton MR spectroscopic cytosolic choline resonance in the anterior cingulate cortex. Comparable data for forty-one depressed subjects participating in imaging trials and treated with open label fluoxetine, 20 mg/day for eight weeks, demonstrated reductions in HDRS scores from 21±4 to 11±6 ($p<0.0001$) (FIG. 1). CDP-choline and fluoxetine were associated with complete responses in 6/12 (50%) and 17/41 (41%) of the subjects, respectively (FIG. 1). In depressed adults, therefore, the antidepressant effects of CDP-choline were comparable to those of fluoxetine.

These data represent the first demonstration that human brain lipid metabolism can be modified using pharmacological strategies, and that, particularly in older adults, treatment is associated with improved cognitive performance. These data demonstrate that therapeutic strategies, using cytosine- and cytidine-containing compounds (e.g., CDP-choline), that are aimed at reversing biochemical alterations are beneficial for the treatment of depression or dysthymia.

Use of Citicoline in a Rodent Model of Depression

The effects of citicoline were examined in the forced swim test (FST), a rodent model of depression. Because citicoline is rapidly converted to cytidine and choline, their effects were also examined in the FST. Citicoline did not have antidepressant effects in rats in the FST over a range of doses (50-500 mg/kg, IP) shown to have neuroprotective effects in experimental ischemia in rodents. In fact, high doses of citicoline appeared to have small pro-depressant effects in this model. Molar equivalent amounts of cytidine (23.8-238 mg/kg, IP) had significant antidepressant effects in the FST, whereas molar equivalent amounts of choline (13.7-136.6 mg/kg, IP) had significant pro-depressant effects. The optimally effective dose of cytidine (238 mg/kg, IP) did not affect locomotor activity or establish conditioned rewarding effects at therapeutic concentrations.

Alcohol or Opiate Abuse or Dependence

Measurement of Brain Phospholipids

Figure 2:
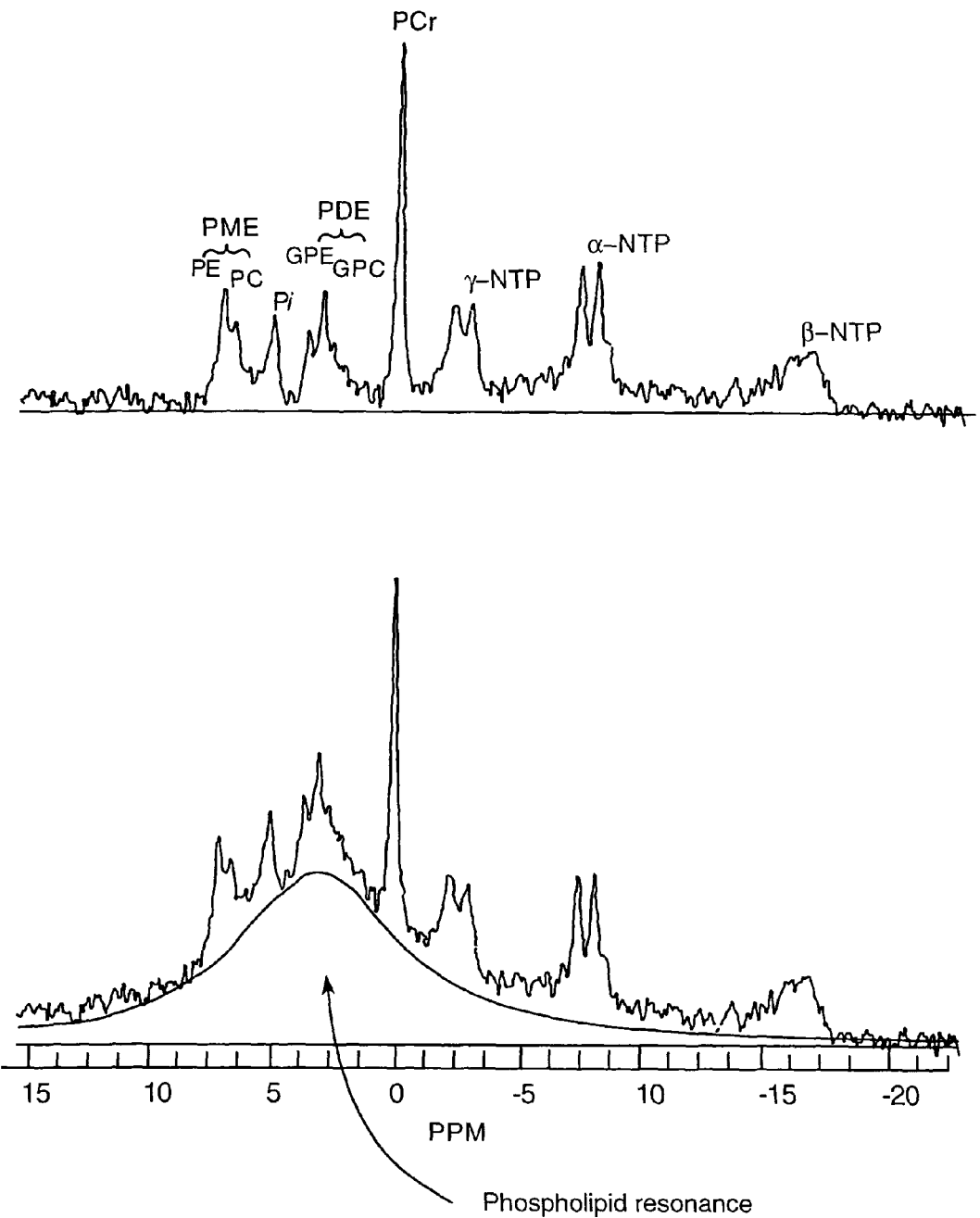
FIG. 2 is a graph showing phosphorus-31 MRS data from the human brain.

The broad component within the phosphorus-31 MR spectrum, arising from human brain phospholipids, may be measured reliably (FIG. 2). Preliminary results indicate that in persons with alcohol and/or opiate dependence, the intensity of this broad phospholipid resonance is decreased by 10-15% relative to values for comparison subjects. Accordingly, therapeutic strategies that are aimed at reversing this biochemical alteration, for example, by increasing phospholipid synthesis, are beneficial for the treatment of alcohol and/or opiate dependence.

CDP-choline Administration Leads to Increased Phospholipid Synthesis

To assess whether chronic CDP-choline administration leads to detectable changes in lipid metabolite resonances in phosphorus-31 MR spectra, eighteen healthy subjects (mean age: 70) were administered 500 mg of an oral formulation of CDP-choline daily for a six week period. From weeks 6 to 12, half of the subjects continued to receive CDP-choline and half received placebo in a double-blind fashion. The MR data demonstrated that CDP-choline treatment was associated with a significant increase in brain phosphodiesters ($p=0.008$), a finding that is indicative of increased phospholipid synthesis. Neuropsychological testing also revealed increases in verbal fluency ($p=0.07$), verbal learning ($p=0.003$), visuospatial learning ($p=0.0001$) across all subjects at week twelve. CDP-choline administration, therefore, improves measures of verbal fluency and spatial memory in healthy adults and results in increased brain phospholipid synthesis in older adults, particularly during chronic administration.

Attention Deficit Hyperactivity Disorder (ADHD)

Functional Magnetic Resonance Imaging of Children Diagnosed with ADHD

A new fMRI procedure (T2 relaxometry or "T2-RT") was developed to indirectly assess blood volume in the striatum (caudate and putamen) of boys 6-12 years of age under steady-state conditions. Six healthy control boys (10.2±1.5 yr) and eleven boys diagnosed with ADHD (9.3±1.6 yr) served as subjects in the study to examine fMRI differences between unmedicated healthy controls and ADHD children on either placebo or the highest dose of methylphenidate. The healthy controls were screened using structured diagnostic interview (K-SADS-E; Orvaschel, H. & Puig-Antich, J., The schedule for affective disorders and schizophrenia for school-age children-epidemiologic version (Kiddie-SADS-E), University of Pittsburgh, Pittsburgh, Pa., 1987), were free of any major psychiatric disorder, and had no more than 3 out of 9 possible symptoms of inattention or hyperactivity-impulsivity by DSM-IV criteria. Children with ADHD were included if they met criteria for ADHD on structured diagnostic interview, and had at least 6 of 9 symptoms of inattention or hyperactivity-impulsivity. Children with ADHD took part in a triple blind (parent, child, rater), randomized, placebo-controlled study of effects of methylphenidate (0, 0.5, 0.8, 1.5 mg/kg in divided dose) on activity, attention, and fMRI. Children with ADHD were treated continuously for one week with placebo or a specific dose of methylphenidate and at the end of the week were tested for drug efficacy using objective measures of attention and activity and fMRI (See Methods) within 1-3 hours of their afternoon dose. The time between dose and testing was held constant for each subject throughout the four treatment conditions. Activity and attention were evaluated in unmedicated healthy controls using the same procedure as children with ADHD, and fMRI followed within the same time frame.

T2 relaxometry, a novel fMRI procedure, was used to derive steady state blood flow measures and to test for enduring medication effects. Although conventional Blood Oxygenation Level Dependent (BOLD) fMRI is a valuable technique for observing dynamic brain activity changes between baseline and active conditions, thus far it has failed to provide insight into possible resting or steady-state differences in regional perfusion between groups of subjects, or to delineate effects of chronic drug treatment on basal brain function. T2 relaxometry, like BOLD, hinges on the paramagnetic properties of deoxyhemoglobin. However, the mismatch between blood flow and oxygen extraction that occurs as an acute reaction to enhanced neuronal activity in BOLD does not persist under steady state conditions. Instead, regional blood flow is regulated to appropriately match perfusion with ongoing metabolic demand, and deoxyhemoglobin concentration becomes constant between regions in the steady-state. Therefore, regions with greater continuous activity are perfused at a greater rate, and these regions receive, over time, a greater volume of blood and a greater number of deoxyhemoglobin molecules per volume of tissue. Thus, there is an augmentation in the paramagnetic properties of the region that is detectable as a diminished T2 relaxation time.

Conventional T2-weighted images provide only a rough estimate of T2, useful for identifying areas of pathology with markedly different T2 properties, such as tumors. To calculate T2-RT with sufficient accuracy to be able to reliably perceive small (ca. 2%) differences in T2 of gray matter associated with functional changes in blood volume, we used fast echoplanner imaging to establish a signal intensity decay curve based on 32 sequential measures at different echo times. For each of the 32 images, a refocused spin echo was observed.

Highly accurate laboratory-based measures of activity and attention were obtained by having the children perform a computerized vigilance test while an infrared motion analysis system captured and recorded movements (see Methods). These findings were used to ascertain associations between regional measures of T2-RT and capacity to inhibit motor activity to low levels while attending to a monotonous but demanding task.

As expected, boys with ADHD on placebo did not sit as still as healthy controls during the attention tests. They spent more time moving (temporal scaling: $F_{1,14}=9.42$, $P=0.008$) and had less complex movement patterns (spatial scaling: $F_{1,14}=9.68$, $P=0.008$). On the continuous performance task (CPT), a measure of attention, children with ADHD were less accurate (92.0% vs. 97.1%; $F_{1,14}=2.94$, $P=0.10$), and had a more variable response latency ($F_{1,14}=3.11$, $P<0.10$), though these differences did not reach statistical significance in this limited sample.

Figure 3B:
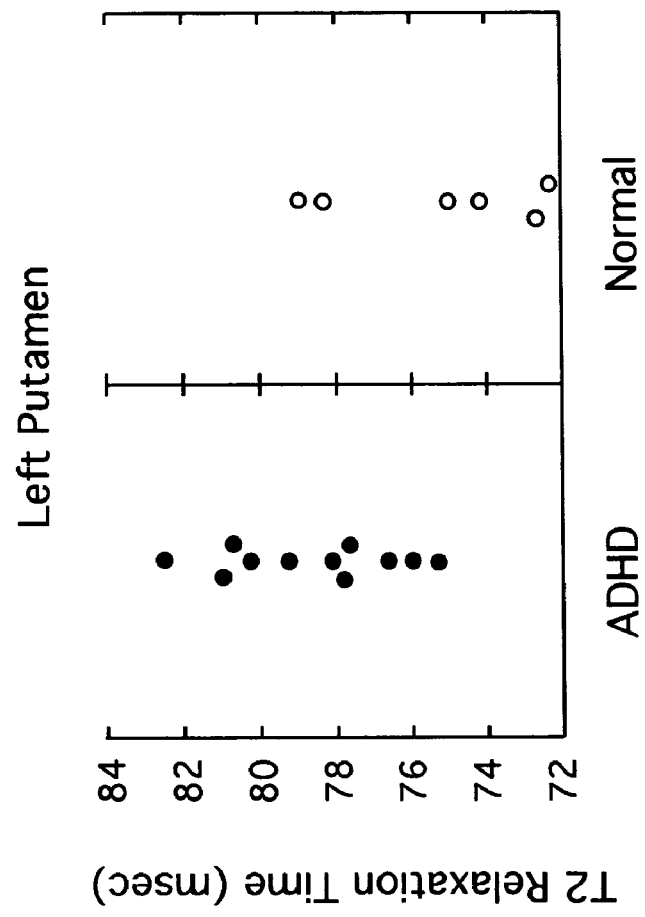
FIG. 3B is a scatter plot of individual T2 relaxation times for the right putamen of ADHD children treated with placebo and of healthy children. The increased T2 relaxation times seen in the ADHD sample indicate diminished regional blood volume.

Differences in the caudate and putamen regions of children with ADHD and healthy controls, as well as the change in the T2-RT in these regions in response to methylphenidate, were also studied by imaging. The thalamus was evaluated as a contrast region in which group differences or drug effects were not expected. No significant differences emerged between ADHD children on placebo and healthy controls in bilateral T2-RT measures for the caudate nucleus ($F_{1,14}=2.80$, $P=0.12$). In contrast, ADHD children and controls differed markedly in bilateral putamen T2-RT measures (77.9±1.1 msec vs. 76.1±1.1 msec; $F_{1,14}=9.40$, $P=0.008$). On average, T2-RT was 3.1% higher in ADHD children than in controls in the left putamen ($F_{1,14}=14.5$, $P=0.002$; FIG. 3B) and 1.6% higher in the right ($F_{1,14}=2.62$, $P=0.13$).

For healthy controls and ADHD children on placebo, there were marked and significant correlations between motor activity and T2-RT for the putamen bilaterally, but not for caudate or thalamus (Table 1A). Temporal scaling and average time spent immobile, two measures of activity-inactivity, correlated −0.752 ($P<0.001$) and −0.730 ($P<0.001$), respectively with T2-RT in putamen. The complexity of the movement pattern also correlated with T2-RT in putamen ($r_s=0.630$, $P<0.01$). Similarly, in unilateral analyses, all three motor activity measures correlated with T2 measures for both right and left putamen (Table 1A).

Figure 4A:
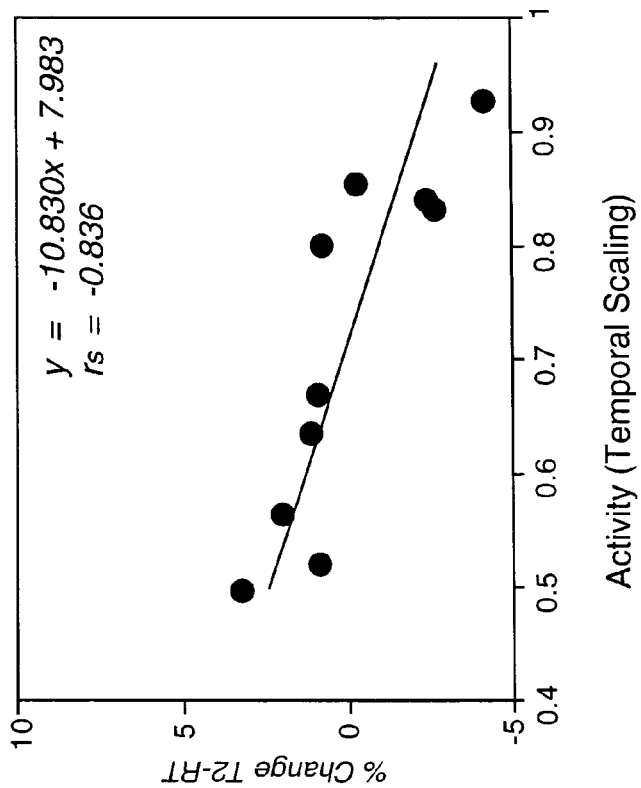
FIG. 4A is a graph showing the association between T2-RT in right putamen and accuracy on the performance of the computerized attention task for children with ADHD on placebo (closed circles) and normal controls (open circles). As indicated there is a significant inverse linear correlation between accuracy and T2 relaxation time (higher levels of T2-RT indicate lower perfusion).

There were also robust correlations between measures of CPT performance and T2-RT in the putamen bilaterally (Table 1B). Accuracy on the CPT correlated −0.807 ($P<0.0001$) with T2-RT, while variability (S.D.) in response latency correlated 0.652 ($P<0.005$). These associations were observed in both right and left putamen (Table 1B, FIG. 4A). In addition, there was also a significant association between accuracy on the CPT task and T2-RT for right, but not left, thalamus. As indicated in FIG. 4A, there is a significant inverse linear correlation between accuracy and T2 relaxation time (higher levels of T2-RT indicate lower perfusion).

Methylphenidate exerted robust effects on attention, enhancing performance accuracy ($F_{1,10}=5.98$, $P<0.05$) and reducing response variability (S.D.) from 242 to 149 msec ($F_{1,10}=14.5$, $P<0.005$). Methylphenidate also exerted significant effects on activity, producing a 126% increase in time spent immobile ($F_{1,10}=5.47$, $P<0.05$), and increasing the complexity of the movement pattern ($F_{1,10}=5.73$, $P<0.05$). However, drug effects on activity were strongly dependent on the subject's unmedicated activity level. For instance, spatial complexity increased 52.6% in the 6 subjects who were objectively hyperactive (at least 25% more active than normal controls) on placebo ($F_{1,5}=13.16$, $P<0.02$), but was unaffected (<8% increase) in the 5 ADHD children who were not ($p>0.6$).

Figure 4B:
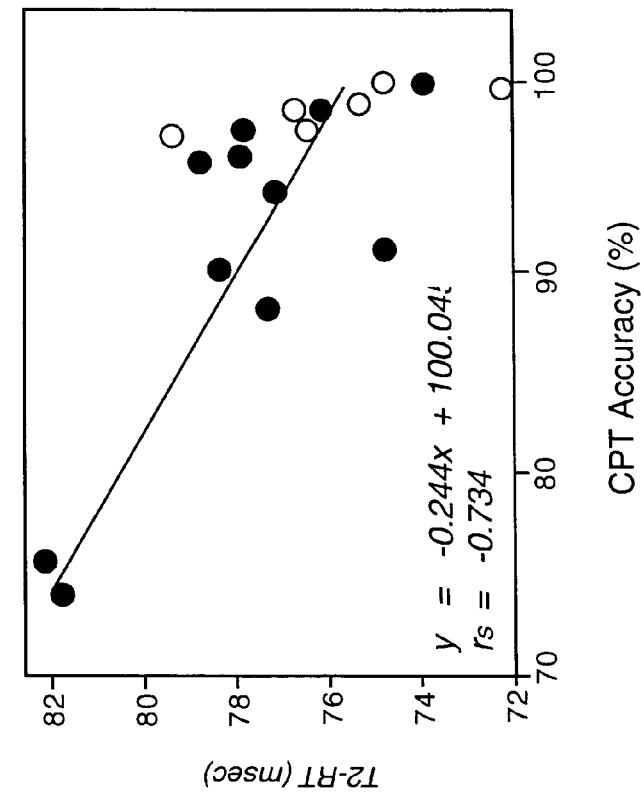
FIG. 4B is a graph showing the percent change in T2-RT in the right putamen following treatment with methylphenidate in children with ADHD. Note that the degree of response is affected by the baseline level of activity. The higher the temporal scaling the greater the activity of the subject. T2-RT change values below zero indicate enhanced regional blood volume following methylphenidate administration.

T2-RT in both right and left putamen were significantly altered by ongoing treatment with methylphenidate (ANCOVA: $F_{1,9}=12.81$, $P=0.006$), although the response was strongly tied to the subject's unmedicated activity state (Drug×temporal scaling covariant $F_{1,9}=11.09$, $P=0.008$; FIG. 4B). Methylphenidate failed to exert significant effects on T2-RT in thalamus ($F_{1,9}=0.13$, $P>0.7$). A trend-level difference was observed in the right caudate ($F_{1,9}=3.85$ $P=0.08$).

Overall, as higher T2-RT corresponds to lower perfusion, the present findings of increased T2-RT in the putamen of children with ADHD, and the correlation between T2-RT and objective markers of disease severity, are consistent with some earlier studies. Furthermore, the present findings also suggest that a considerable proportion of the variance between subjects in degree of hyperactivity and inattention can be accounted for by T2-RT differences within the putamen alone.

In summary, boys with ADHD (n=11) had higher T2 relaxation time (T2-RT) measures in putamen bilaterally than healthy controls (n=6; $P=0.008$). Relaxation times correlated with the child's capacity to sit still ($r_s=-0.75$, $P<0.001$), and his accuracy in performing a computerized attention task ($r_s=-0.81$, $P<0.001$). Blinded, placebo-controlled daily treatment with methylphenidate significantly altered T2-RT in the putamen of children with ADHD ($P=0.006$), though the magnitude and direction of the effect was strongly dependent on the child's unmedicated activity state. A similar but non-significant trend was observed in the right caudate. T2-RT measures in the thalamus did not differ significantly between groups, and were not affected by methylphenidate.

Methods

Assessment of Activity and Attention. Activity and attention data were collected as previously described (Teicher et al., J. Am. Acad. Child Adolesc. Psychiatry 35: 334-342, 1996). In brief, children sat in front of a computer and were evaluated using a simple GO/NO-GO CPT in which the subject responds to visual presentation of a target and withholds response to a non-target stimuli that appear in the center of the screen at a fixed 2 second inertial interval (Greenberg et al., Psychopharmacol. Bull. 23: 279-282,1987). The stimuli are simple geometric shapes that can be distinguished without right/left discrimination, and are designed to allow children with dyslexia to perform as well as normal controls. Three 5-minute test sessions were recorded during a 30-minute test period while an infrared motion analysis system (Qualisys, Glastonbury, Conn.) recorded the movement of small reflective markers attached to the head, shoulder, elbow, and back of the child. The motion analysis system stored the precise vertical and horizontal position of the centroid of each marker 50 times per second to a resolution of 0.04 mm.

Results were analyzed using the concept of "micro-events." A new micro-event begins when the marker moves 1.0 millimeters or more from its most recent resting location, and is defined by its position and duration. The spatial scaling exponent is a measure of the spatial complexity of the movement path, and is calculated from the logarithmic rate of information decay at progressively lower levels of resolution. The temporal scaling exponent is a scale invariant stochastic measure of percent time active. Values range from 0 (immobility) to 1 (incessant activity), and are calculated from the slope of the log-log relationship between the duration of micro-events and their frequency (Paulus et al., Neuropsychopharmacology 7:15-31, 1992). Software for presenting stimuli, recording activity, and analyzing results was written by M. Teicher and licensed to Cygnex Inc.

T2 Relaxometry fMRI Procedure and Relaxation Time Computations.

Children were positioned in the scanner and instructed to remain as still as possible. Images were acquired using a 1.5-T magnetic resonance scanner (Signa, General Electric Medical Systems, Milwaukee, Wis.) equipped with a whole-body, resonant gradient set capable of echo planar imaging (Advanced NMR Systems, Inc., Wilmington, Mass.), and a standard quadrature head coil for image detection. During each examination, 3 categories of images were obtained: (1) Scout images (typically T1-weighted sagittal images); (2) High resolution T1-weighted matched axial images through the ten planes for which maps of T2 were generated; and (3) 32 spin echo, echoplanar image sets, with TE incremented by 4 msec in each consecutive image set (e.g., TE (1)=32 msec, TE (2)=36 msec, ... TE (32)=160 msec) through the same ten axial planes (TR=10 sec, Slice thickness=7 mm with a 3 mm skip, in-plane resolution=3.125 mm×3.125 mm, FOV=200 mm). The 32 TE-stepped images were then transferred to an off-line workstation and corrected for in plane motion using a modification of the DART image registration algorithm (Maas et al., Magn. Reson. Med. 37:131-139, 1997). The value of T2-RT was then estimated on a pixel-wise basis by linear regression of the signal intensity $S(x,y,n)$ assuming an exponential decay of $S(x,y,n)$ with time constant $T2\text{-}RT(x,y)$, such that $\ln S(x,y,TE(n)) = \ln S(x,y,TE=0) - (TE(n)/T2\text{-}RT(x,y))$, where $(x,y)$ is the pixel position and $TE(n)$ is the spin-echo time corresponding to the nth image of the series.

Figure 3A:
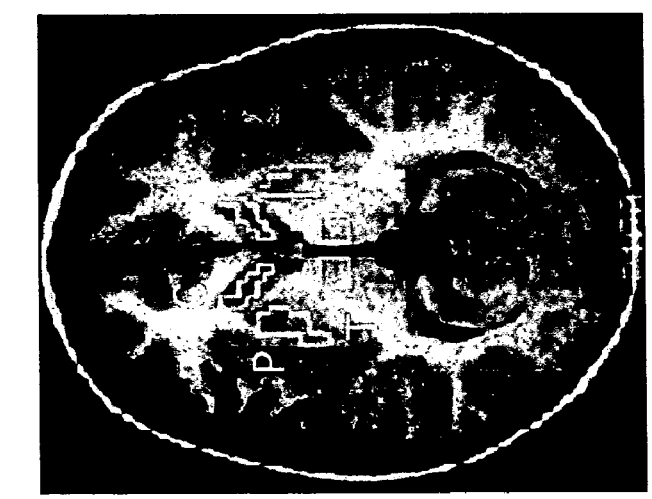
FIG. 3A is a T1 weighted anatomical image of the basal ganglia and thalamus, indicating regions of interest, used to sample the T2 relaxation times, for C (caudate), P (putamen), and T (thalamus).

Calculations of regional T2-RT were made for left and right anterior caudate, putamen, and thalamus (as a contrast region) using anatomic boundaries observed in T1 weighted images and conservatively circumscribed to avoid encroaching into ventricular space (see FIG. 3A for regions of interest). Delineation of regions and analysis of imaging data was performed on coded images, and the responsible researcher was blind to the identity, diagnosis, or treatment condition of the subject. T2-RT was calculated from the median value of all the designated pixels, as the median provides a regional estimate less susceptible to contamination by spurious values from bordering white matter and cerebrospinal fluid regions than the mean.

The intrinsic reliability of the T2-RT measure was determined using a within subject procedure with head repositioning when necessary. There was a lag between end of the first session and start of the second session of ca. 5 minutes. Based on 8 within-session comparisons with normal adult volunteers we observed a correlation of 0.942, and an average mean value difference of −0.17% for T2-RT of the putamen.

Statistical Analyses. Differences between groups was assessed using ANCOVA with age as a covariate. Although the groups did not differ significantly in age, the behavioral and fMRI measures showed age-dependent changes, and ANCOVA minimized this component of the error variance. Correlations were calculated using Spearman Rank-Order test. Differences between behavioral and FMRI measures of ADHD subjects on methylphenidate vs. placebo were assessed using repeated measure ANCOVA with placebo activity (temporal scaling) as a covariate. This was crucial in the analysis, as methylphenidate effects are strongly rate-dependent, and basal activity on placebo accounted for ca. 50% of the magnitude of the medication effect.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the appended claims.

The invention claimed is:

1. A method of treating attention-deficit hyperactivity disorder (ADHD), comprising administering to a mammal diagnosed with ADHD a therapeutically-effective amount of a compound selected from the group consisting of a cytidine-containing compound and a cytosine-containing compound, wherein said compound is administered in a pharmaceutical formulation.

2. The method of claim 1, wherein said cytidine-containing compound is cytidine and is administered.

3. The method of claim 1, wherein said cytidine-containing compound further comprises choline and is administered.

4. The method of claim 1, wherein said cytidine-containing compound is cytidine diphosphate (CDP)-choline and is administered.

5. The method of claim 1, wherein said cytidine-containing compound is CDP and is administered.

6. The method of claim 4, wherein said CDP-choline is administered orally.

7. The method of claim 1, wherein said administering comprises administration of more than one dose.

8. The method of claim 1, wherein said mammal is a human.

9. The method of claim 8, wherein said human is a child or adolescent.

10. The method of claim 8, wherein said human is an adult aged 60 years or older.

\* \* \* \* \*